US005592759A

United States Patent [19]

Cox

[11] Patent Number: 5,592,759

[45] Date of Patent: Jan. 14, 1997

[54] VIBRATING FOOTWEAR

[75] Inventor: Donald R. Cox, Chesterfield, Mo.

[73] Assignee: Co-Jo Sports, Inc., Ellisville, Mo.

[21] Appl. No.: 378,560

[22] Filed: Jan. 26, 1995

[51] Int. Cl.$^{6}$ .............................. A61F 5/14

[52] U.S. Cl. .............................. 36/141; 36/136

[58] Field of Search .............................. 36/141, 136, 132, 36/137

[56] References Cited

U.S. PATENT DOCUMENTS

| | | | |
|---|---|---|---|
| 2,931,893 | 4/1960 | Gonzalez Arias et al. | 36/137 X |
| 2,949,108 | 8/1960 | Vecchio | 128/24.1 |
| 3,273,264 | 9/1966 | Farinello, Jr. | 36/3 A |
| 3,731,674 | 5/1973 | Parvin | 128/25 B |
| 3,800,133 | 3/1974 | Duval | 36/137 X |
| 3,888,242 | 6/1975 | Harris et al. | 128/64 |
| 4,173,216 | 11/1979 | Nolet | 128/24.1 |
| 4,507,877 | 4/1985 | Vaccari et al. | 36/2.6 |
| 4,510,704 | 4/1985 | Johnson | 36/136 |
| 4,694,839 | 9/1987 | Timme | 128/721 |
| 4,802,463 | 2/1989 | Rojas | 128/36 |
| 4,845,865 | 7/1989 | Chang et al. | 36/136 |
| 5,029,575 | 7/1991 | Zhivotchenko | 128/25 B |
| 5,113,850 | 5/1992 | Larremore et al. | 128/32 |
| 5,159,768 | 11/1992 | Longo, Jr. | 36/139 |
| 5,269,081 | 12/1993 | Gray | 36/136 |
| 5,438,488 | 8/1995 | Dion | 36/137 X |

FOREIGN PATENT DOCUMENTS

| | | | |
|---|---|---|---|
| 2556190 | 6/1985 | France | 36/137 |
| 2675025 | 10/1992 | France | 36/137 |
| 3842913 | 6/1990 | Germany . | |
| 1653724 | 6/1991 | U.S.S.R. . | |

OTHER PUBLICATIONS

Shiatsu™ massagers instruction manual.

*Primary Examiner*—Ted Kavanaugh
*Attorney, Agent, or Firm*—Heller & Kepler

[57] ABSTRACT

An article of footwear made to vibrate by either of two types of vibrating motive members and associated with the structure of the shoe to transmit the vibrations generated to the foot of the wearer. Two vibrating motive members are described, a motor having an off-center shaft-mounted weight and pulsating-type motor.

11 Claims, 5 Drawing Sheets

①

②

③

VIBRATING FOOTWEAR

BACKGROUND OF THE INVENTION

The invention disclosed herein relates in general to vibrating footwear, namely a shoe, and more particularly to a vibrating shoe. The vibrating shoe of this invention is an improvement over the conventional constructions in which vibrations are typically created with a motor having an off-center, shaft mounted weight.

The vibrating shoe of the present invention is an improvement over previous vibrating and massaging shoes in that the motor, power source and actuator are all combined into one unit which does not necessarily mount directly to the shoe assembly. This results in a motor unit which can be removed for replacement or repair.

Vibrating shoes have been disclosed as being advantageous for increasing circulation and decreasing discomfort by gently massaging the feet. This type of footwear is particularly advantageous for users/wearers who spend a great deal of time on their feet or who have circulatory problems.

Previously disclosed vibrating footwear has been limited by the use of directly mounted motors and complex vibration transferring systems which are not easily repaired or replaced without complete disassembly or replacement of the footwear.

Accordingly, it is an object of the present invention to provide a vibrating shoe assembly in which the motor, power source and actuation switch are part of a single integral motor unit. With the arrangement and mounting of the motor, power source and actuation switch of this invention it is believed that an improved function of the invention and beneficial results to the user will be obtained.

Another object of the present invention is to provide a vibrating shoe assembly in which an integral motor unit is not directly mounted to the shoe assembly, thereby providing for easy removal and replacement of the motor unit. The construction of the present invention facilitates operation of the vibration creating motor and ease of replacing batteries.

A further object of the present invention is to provide a vibrating shoe in which the integral motor unit is easily accessible and can be removed and replaced without disassembly or disposal of the shoe. The vibrating shoe of the present invention is adapted, therefore, for use for as long as the shoes themselves are serviceable as footwear.

Still another object of the present invention is to provide a vibrating shoe in which the integral motor unit is accessed by removal of a removable inner sole or sock liner. The vibrating shoe of this invention is preferably provided with a unique removable inner sole or sock liner that functions as would any conventional inner sole or sock liner while still allowing the user to easily access the compartment containing the motor and power source.

Still a further object of the present invention is to provide an integral motor unit in which the actuator switch is adapted for operation without physically extending through any portion of the shoe sole. The vibrating shoe of this invention foresees using a reed switch or the equivalent to allow the user to easily access the power switch of the vibrating shoe through the use of an extension member that extends through a portion of the shoe or sole rather than the switch.

Another object of the present invention is to provide an arch projection which enhances transfer of the vibrations to the arch of the user/wearer's foot. The arch projection is adapted to be added to the basic motor, power switch and power source embodiment without any further modifications other than the addition of the arch projection. The curved portion of the arch can extend past the arch and towards the forefoot of the wearer so as to extend the vibration to the forefoot.

A further object of the present invention is to provide alternative power and recharging capabilities for the motor used to develop the vibrations. The motor can be powered by any conventional means, including a rechargeable battery unit or an ac plug adapter.

Another object of the present invention is to provide a vibrating shoe in which secondary or additional vibrating motors are located to directly vibrate the tongue or collar portion of the shoe. These latter embodiments are preferably use in lieu of the motor assembly in the sole portion of the shoe. However, as will become apparent to one skilled in the art, it would also be possible to provide one or more vibrating members, if so desired.

Still another object of the present invention is to provide a shoe in which vibrations are created using a pulsation device.

SUMMARY OF THE INVENTION

To accomplish the foregoing and other objects of this invention there is provided a vibrating shoe assembly. The assembly consists of an otherwise conventional shoe upper in combination with an outer sole, a removable inner sole, and a mid-sole or outer sole shell which houses a vibrating motor assembly.

In a preferred embodiment, the vibrating motor assembly includes a motor having an off-center shaft mounted weight. The assembly is battery powered and has an actuator switch accessible to the user/wearer.

The access switch can be mounted on an external portion of the shoe. In another preferred embodiment, a switch is used that is accessible from outside the shoe even when this switch is located within the mid/outer sole of the shoe.

The internal actuator switch presently preferred is a magnetic reed switch wired and molded into the motor assembly. The switch is activated by a spring loaded magnet plunger which extends from the motor assembly through to the outside of the sole. This allows the user to easily turn the motor on and off without the use of a switch which projects beyond the perimeter of the shoe/sole.

While the motor assembly may be permanently attached to the shoe or sole, in a preferred embodiment the motor assembly is mounted to the underside of an insert portion of the mid-sole upper surface. When the insert is in place, the motor assembly is housed in a cavity in the mid/outer sole. The motor assembly is easily accessed by the user by removing the inner sole or sock liner. This allows the motor assembly to be removed for replacement or repair without dismantling or destroying or discarding the shoe (pair) for a new shoe (pair).

In one embodiment the mid-sole can include an aperture or cavity to house the spring loaded magnet plunger, as disclosed above. This allows the user/wearer to easily activate the motor and turn the vibrating motor on and off without removing the inner sole or sock liner.

In another embodiment the outer sole shell is constructed or provided with an aperture or cavity to house the spring loaded magnet and plunger assembly, as disclosed above. This allows the user/wearer to easily activate the motor and turn the vibrating motor on and off without removing the inner sole or sock liner.

In an alternative embodiment, the mid/outer sole insert portion further includes an arch projection. This projection extends to the user/wearer's arch region, and enhances the transfer of vibrations to this area.

Other alternative embodiments of the motor assembly include having a timer to automatically turn the motor off, using a multispeed motor, or including a fan to cool the motor, thereby prevent overheating. The weight eccentrically attached to the motor shaft can be modified to become an air moving member as the modified weight is rotated by the motor shaft.

In another alternative embodiment the vibrating motor can be replaced by a pulsation device. This device may include a dial to regulate frequency, pulse and amplitude of the pulsations created.

These and other objects and features of the present invention will be better understood and appreciated from the following detailed description of preferred embodiments thereof, selected for purposes of illustration and shown in the accompanying drawings.

DETAILED DESCRIPTION

Figure 1:
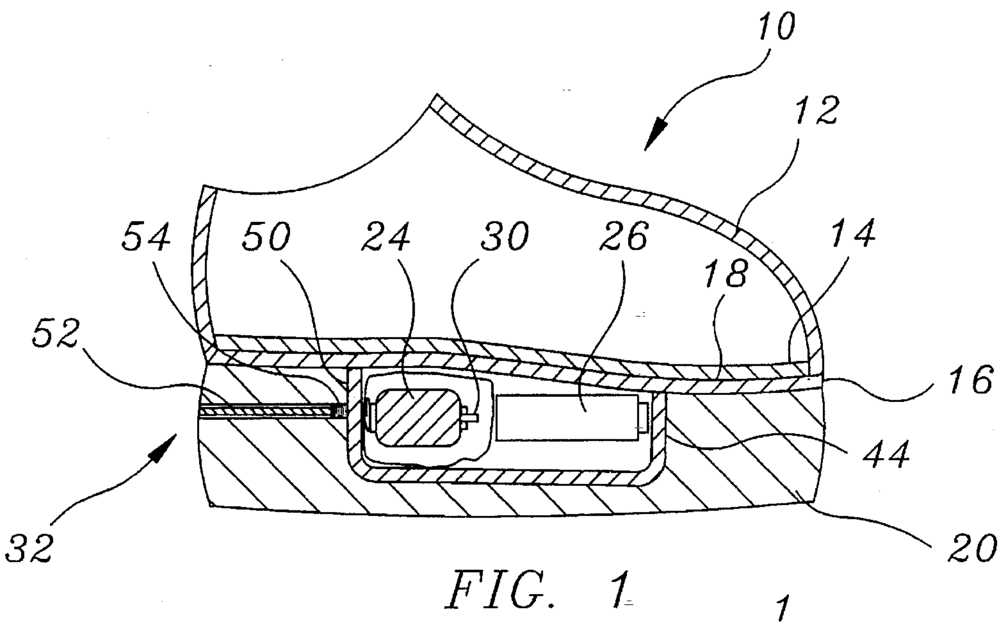
FIG. 1 is a cross-sectional view of a vibrating shoe in accordance with the present invention taken along line 1—1 in FIG. 2.
Figure 2:
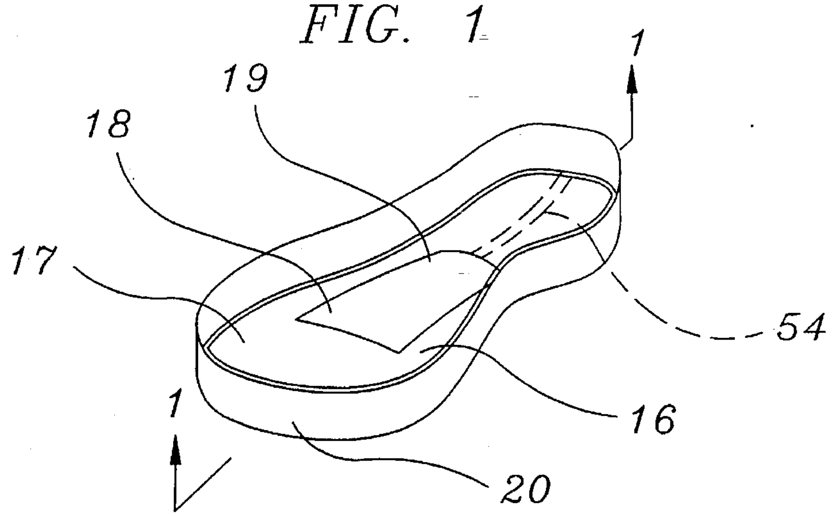
FIG. 2 is a perspective view of the mid-sole, mid-sole insert and motor assembly of the invention of FIG. 1, the position of the spring-loaded magnetic plunger being show in dashed lines.
Figure 3:
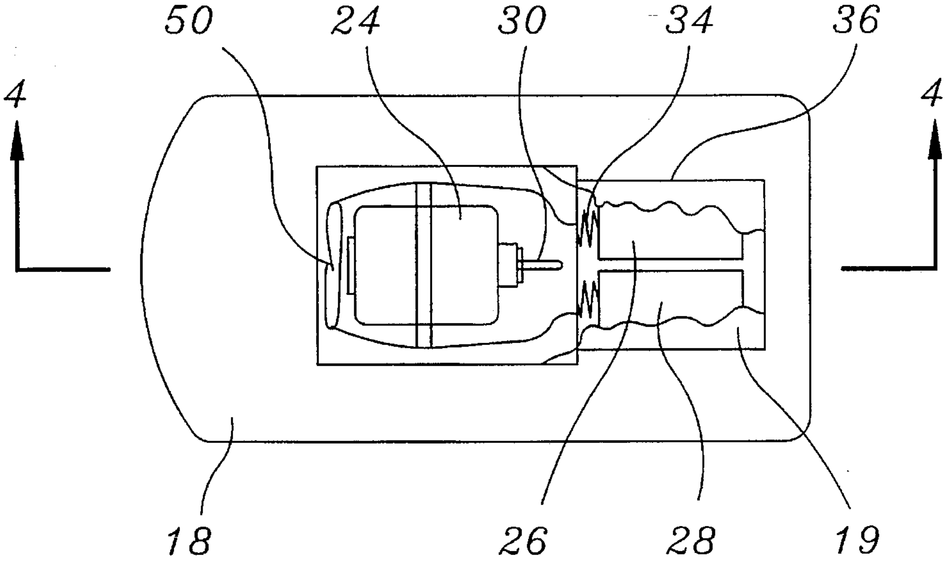
FIG. 3 is a plan view of the mid-sole and motor assembly of the invention of FIG. 1, the mid-sole insert being broken away to more clearly illustrate the motor assembly location, including a bifurcated cavity to house the battery and motor, in an alternative embodiment of the outer sole cavity.

Referring now to the drawings there is shown a preferred embodiment for the vibrating footwear of the present invention. The vibrating footwear of the present invention is particularly adapted for providing a massaging action and stimulating circulation in the foot without removing the shoe.

FIG. 1 illustrates the vibrating footwear device generally designated 10. The preferred embodiment shown includes a conventional upper 12, a removable inner sole 14, a mid-sole 16 and an outer sole 20. The shoe may be constructed by any suitable means. The shoe construction may be of a board lasted or perimeter board construction, and the sole portions of the shoe may be constructed of any suitable material, including leather, rubber, plastic or foam. These methods of construction are well known to those skilled in the art and will not therefore be discussed in detail.

The embodiment illustrated may further include a removable sock liner and an insole board 17. The sock, which acts as a buffer between the foot and insole board may be full (heel to toe) or a half lining (heel to front of shank).

Figure 4:
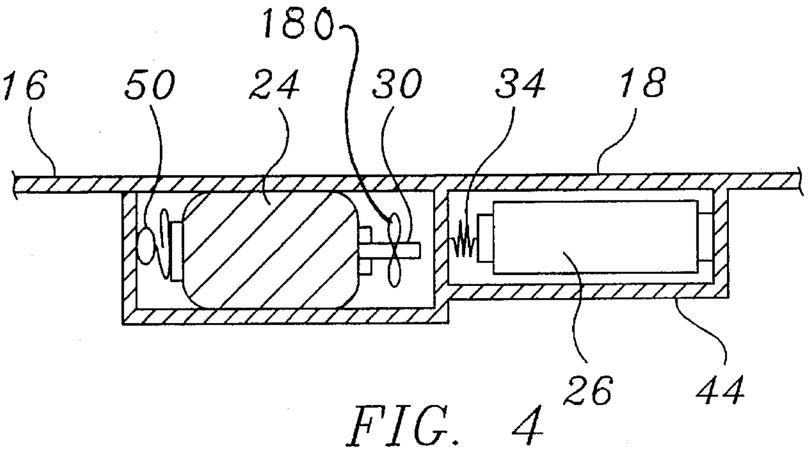
FIG. 4 is a cross-sectional view of the mid-sole and motor assembly of the invention of FIG. 3 taken along line 4—4 in FIG. 3.

The mid-sole 16 or outer sole (depending upon the construction, i.e., mid-sole/outersole or shell outersole, hereinafter referred to generally as mid/outer sole) receives a motor assembly 18 which allows access to the motor, battery and switch assembly, generally designated 22. Motor assembly 18 can be mounted or affixed to the shoe/sole by any suitable method. As shown in FIG. 4, in a preferred embodiment the motor assembly 18 is mounted with the assembly 22 mounted on the underside of a vibration transmitting member 19. The assembly 22 is mounted to member 19 in any conventional manner.

In the preferred embodiment, the insert portion 18 is removable from the mid/outer sole 16, and is not directly mounted to the mid/outer sole 16. When the insert portion 18 is in place there is provided a smooth and stable surface to support the inner sole or sock liner 14 and the user/wearer's foot.

Figure 12:
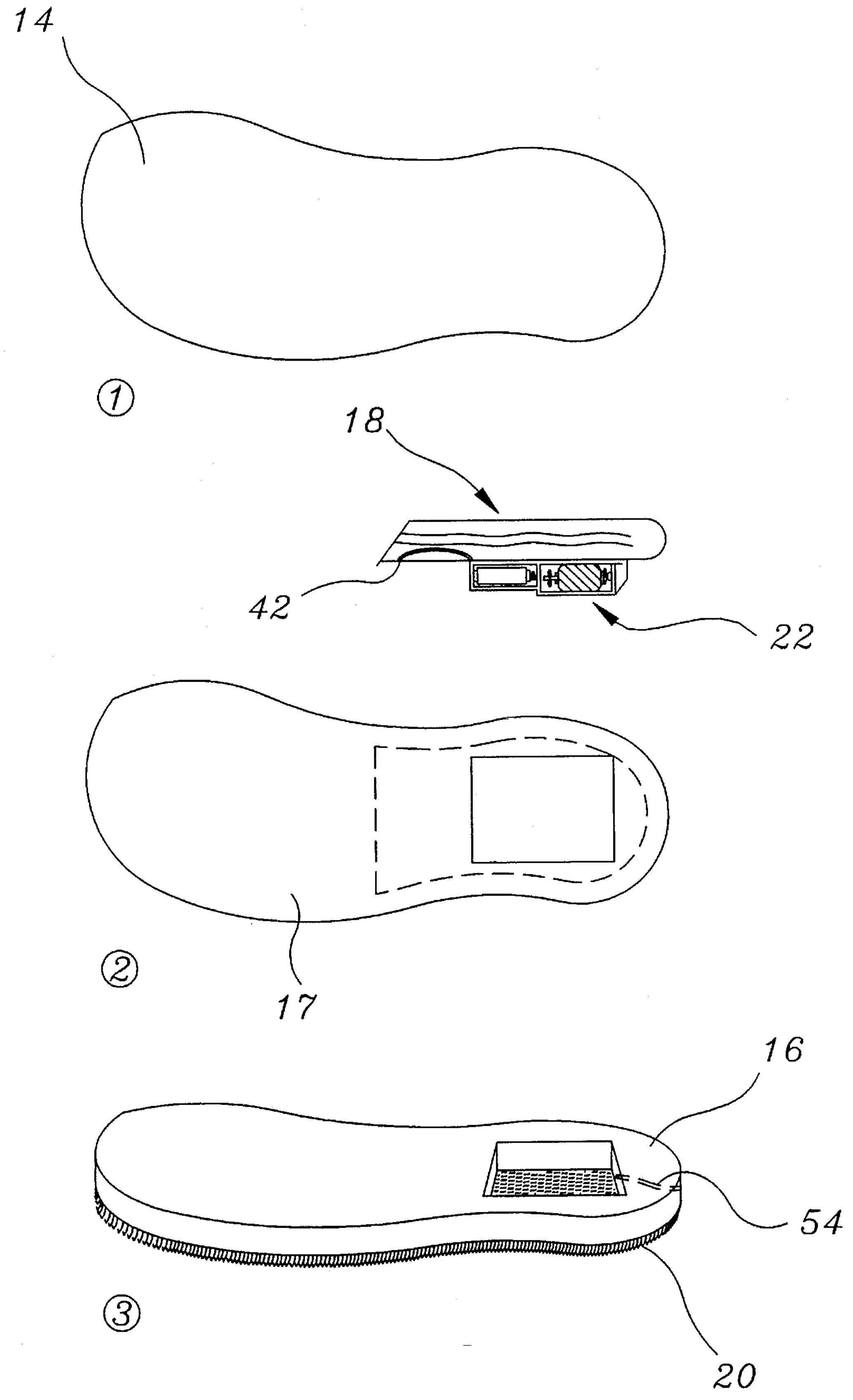
FIG. 12 is an exploded diagrammatic view of one preferred embodiment of the present invention illustrating the relationship of sock liner, insole board, mid-sole (rather than outer sole shell) and outsole.

A diagram of the mid-sole and sock liner shoe construction embodiment is shown in an exploded view in FIG. 12. It will be understood by those skilled in the art that a removable insole can be replace the removable sock liner and an outer sole shell can replace the mid-sole and outsole construction illustrated in FIG. 12 as an equivalent shoe construction.

In a preferred embodiment, the integral assembly 22 includes a vibrating motor 24, two batteries 26, 28, and an actuator means, generally designated 32. These elements are connected by conventional electrical circuitry 34, which is constructed as part of the outer motor housing 44.

In a preferred embodiment and the alternative embodiments as well, except for the embodiments incorporating a pulsating type motor, the motor vibrations are caused by an off-center shaft mounted weight 30, and the actuator means 32 is a magnetic reed switch 50, in combination with a loaded magnetic plunger 52 extends through an aperture or cavity 53 in the outer sole 20. This actuator arrangement allows operation of the motor switch without any portion extending beyond the shoe sole. FIG. 4 shows the shaft mounted weight 30 comprising a fan blade 180 which serves as a self-cooling fan.

The outer sole includes a cavity 36 to house the motor assembly. FIG. 1 illustrates a bifurcated motor assembly cavity. The cavity, however, may be formed of any size and shape which will accept the motor assembly and provide the necessary clearance for the desired vibration of the motor. When the insert portion 18 is placed into the mid-sole or outer sole shell 16, the assembly 22 depends from the motor assembly 18 into the midsole or outersole shell cavity 36.

The removable inner sole or sock liner 14 provides access to the cavity in either the mid-sole or the outersole shell for the motor assembly 18. The removable inner sole or sock liner 14, in conjunction with the motor assembly 18, allows removal of the assembly 22 for repair or replacement without disassembly of the entire shoe.

This is accomplished by removing the inner sole or sock liner 14 to expose motor assembly 18. Motor assembly 18 and its depending assembly 22 call then be lifted out as all integral unit.

Figure 5:
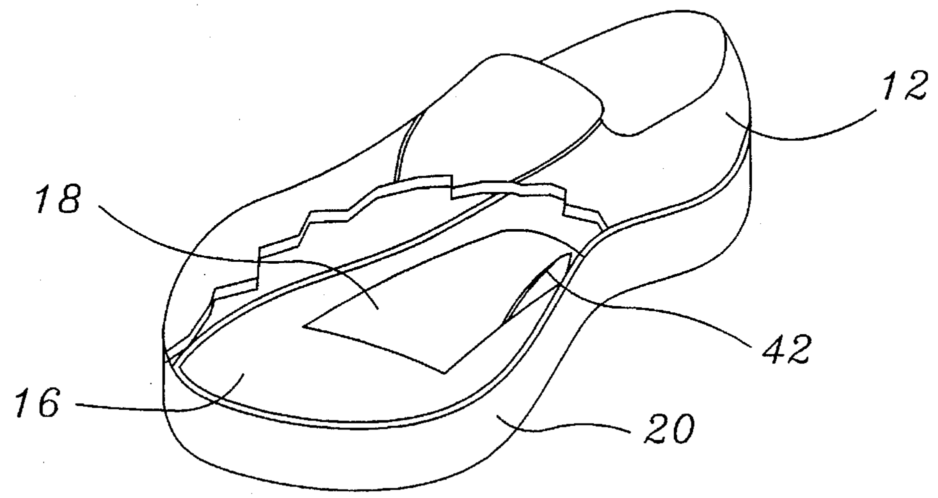
FIG. 5 is a perspective view of an alternative embodiment of the mid-sole and motor assembly of the invention of FIG. 1, the illustrated embodiment including an arch projection.
Figure 6:
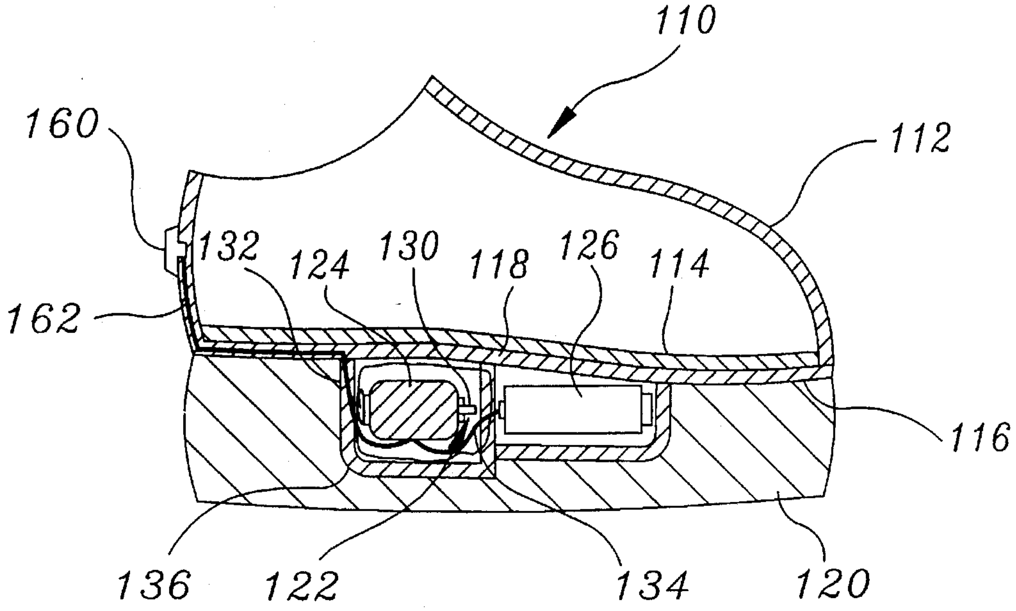
FIG. 6 is a cross-sectional view of an alternative embodiment of the present invention taken along line 6—6 in FIG. 7.
Figure 7:
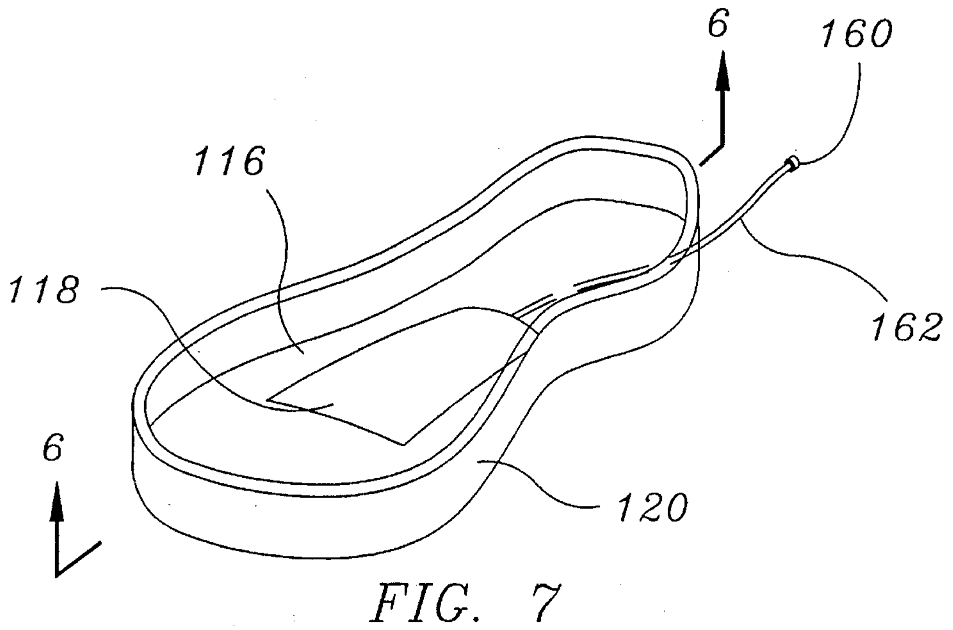
FIG. 7 is a perspective view of the mid-sole, mid-sole insert and outer sole of the invention of FIG. I illustrating the actuator switch lead wires.
Figure 8:
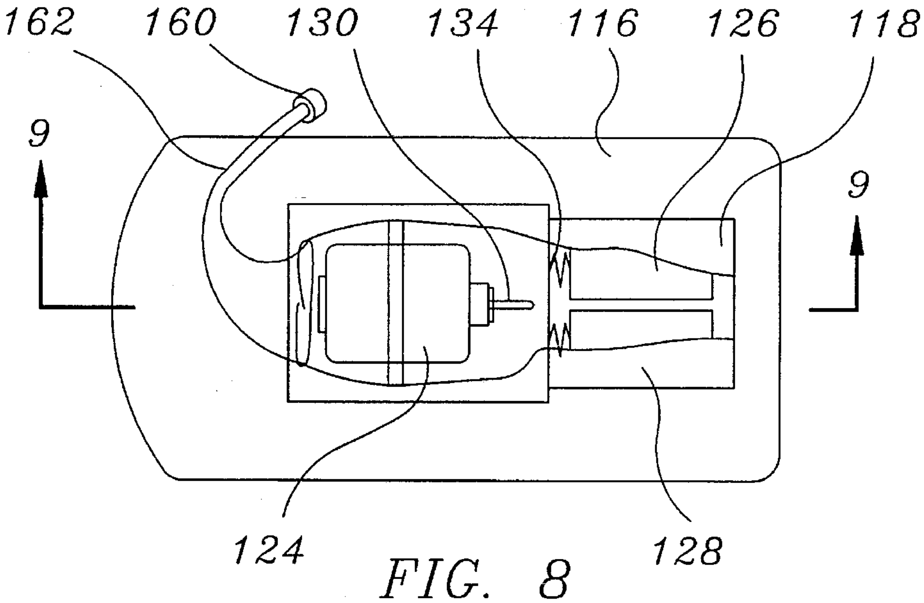
FIG. 8 is a plan view of the mid-sole, actuator lead wires and motor assembly of the invention of FIG. 6, the mid-sole insert being broken away to more clearly illustrate the motor assembly location, including a bifurcated outer sole cavity to house the battery and motor.
Figure 9:
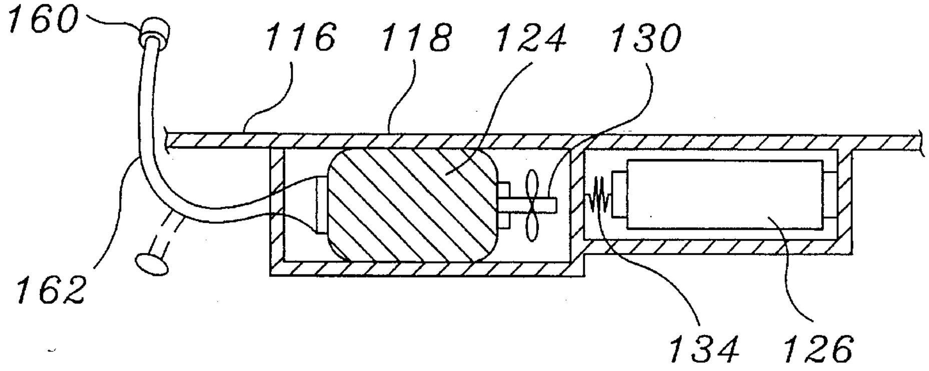
FIG. 9 is a cross-sectional view of the mid-sole and motor assembly of the invention of FIG. 6 taken along line 9—9 in FIG. 8.
Figure 10:
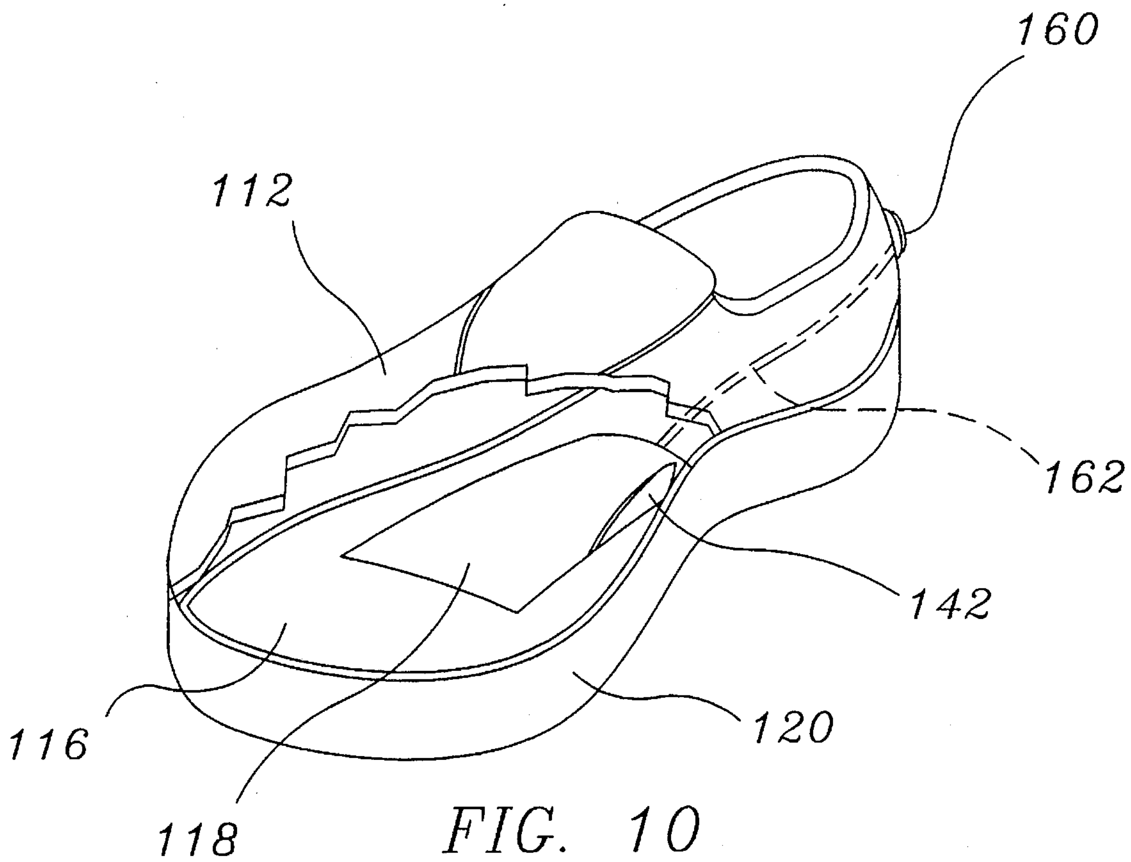
FIG. 10 is a perspective view of an alternative embodiment of the mid-sole and motor assembly of the invention of FIG. 6, the illustrated embodiment including an arch projection.

In the alternative embodiment illustrated in FIG. 5, the motor assembly 18 further includes an arch projection 42. Projection 42 extends upward to the general location of the user/wearer's arch. This enhances the transfer of the motor vibrations to the arch area of the user/wearer's foot, thereby stimulating increased circulation.

Arch projection 42 can be made of any shape which effectively and comfortably fits against the user/wearer's arch through the shoe, and is appropriately sized for the type and size of shoe being used. As illustrated, the addition of the arch projection does not require any further modifications of the motor assembly or shoe design, other than the addition of the arch projection itself.

In the alternative embodiment illustrated in FIGS. 6 through 10, the vibrating footwear device generally designated 110 illustrates an alternative activation switch. As described for the embodiment disclosed above, this embodiment includes a conventional upper 112, a removable inner sole or sock liner 114, a mid-sole and outsole or outersole shell 116, 120 either one having a cavity 136 for receiving a motor assembly 118.

All assembly 122 depending from a vibration transfer member 119 includes a vibrating motor 124, two batteries 126, 128 and all energizing means 132, connected by circuitry 134.

In this embodiment, the energizing means 132 is connected by lead wires 162 to all external switch 160. Presently preferred is placement of the switch 160 near the rear collar area of the shoe upper 112. This placement provides a switch which is easily accessible to the user, but does not result in any protrusions to interfere with movement of the shoe in use. The timer is shown by the dash-lines in FIG. 9.

Figure 11:
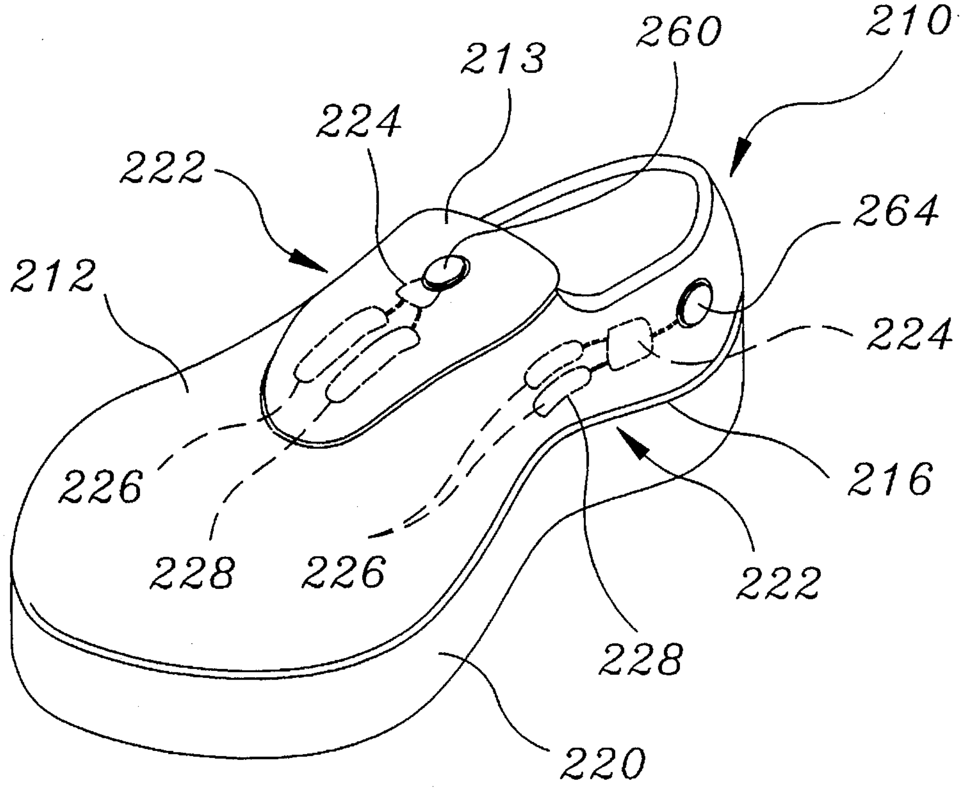
FIG. 11 is a perspective view of an alternative embodiment of the present invention illustrating additional or secondary vibrating motor assemblies located in the tongue and collar portion of the shoe upper.

FIG. 11 illustrates another alternative embodiment in which a pulsating type motor is inserted into a either a collar portion or a tongue portion of the shoe. These pulsating motors can be powered from a battery and energized from an assembly similar to or the same as 22 or 122.

The battery assembly is similar to the battery, assembly for the shaft mounted off-centered weighted motor shaft mounted as shown in the preceding drawing figures. Similarly, the batteries (or battery) may be re-chargeable or the pulsating motor may be powered in any of the same ways already discussed.

It should now be understood by one skilled in the art that the pulsating motor may be used in a shoe either by itself or as all additional or secondary motor assembly added to the shoe upper in addition to the off center weighted motor shaft already described. These additional motor assemblies either provide vibration, if used by themselves or can be expected to enhance vibrations on the upper and rear portions of the user/wearer's foot.

The shoe, generally designated 210, consists of an upper 212, mid-sole 216 and outer sole 220. The shoe 210 and the motor assembly concealed within the outer sole 220 are constructed as described fully in the embodiments disclosed above.

In addition to the motor assembly housed within the outer sole 220, this embodiment includes motor assemblies generally designated 222 at the tongue 213 and collar 215 portions of the shoe 210. The motor assemblies include vibrating motors 224 connected by appropriate wiring to batteries 226, 228 in a cavity as described above. The tongue 213 and collar 215 motor assemblies are activated by switches 260 and 264 respectively.

The switch can be located as shown in the drawings. The modified reed switch or its equivalent can also be used as can any other suitable energizing means.

For comfort purposes, the motor assemblies 222 are the pulsating motor referred to above and can be found in the pulse massagers, for example, sold by SHARPER IMAGE. It may also be possible to obtain miniature versions of the motor assembly 22, which has been described in detail. While a smaller motor, either pulsating or an equivalent, will likely result in weaker vibrations, it is believed that this modification will also provide a comfortable, usable pair of shoes.

The motor assembly 222 located in the collar 215 portion of the shoe may also include a rope or other projection, not shown, which extends from the motor assembly 222 around the collar 215 portion of the shoe. This rope or projection would facilitate transfer of the motor vibrations around the entire shoe collar.

In an alternative embodiment, not shown, the motor assembly may include a timing mechanism to allow the user/wearer to set the motor to shut off after a predetermined time period. In addition, the motor assembly may include a self-cooling fan or ventilation ports to prevent overheating of the motor while providing for ventilation of the wearer's foot.

The pulsation device embodiment may preferably include a dial or other means to regulate the frequency, speed and amplitude of the pulsations created. These controls are often found in association with the pulsation motors in their other uses as previously set forth.

From the foregoing description those skilled in the art will appreciate that all of the objects of the present invention are realized. A vibrating shoe is provided which includes an integral motor, power means and actuator assembly. In a preferred embodiment the integral motor assembly is not directly mounted to the shoe.

A motor assembly is provided which is easily accessed by removal of an inner sole, to allow replacement or repair of the motor assembly without dismantling or destruction of the shoe. An actuator switch provided is easily accessed by the user/wearer without disassembly of the shoe. The actuator switches disclosed further do not project beyond the shoe/sole, and therefore do not interfere with the mobility of the shoe.

An alternative embodiment described includes an arch projection which provides for enhanced transfer of vibrations to the arch area of the user/wearer without modification of the motor assembly or shoe design.

A vibrating shoe is provided in which additional or secondary miniature motor assemblies are included in the tongue and collar portions of the shoe to provide enhanced vibrations to the upper portion of the users/wearer's foot.

While a specific embodiment has been shown and described, many variations are possible. While a conventional shoe upper has been illustrated, any suitable shoe, sandal or boot upper may be utilized, including walking, running, casual or working shoes, slippers, dress shoes, hi-heel, hi-top, or athletic shoes, and roller blade, hiking or skiing boots.

A motor assembly utilizing an off-center shaft mounted weight is presently preferred, but any vibrating motor may be used. The motor can be powered by any conventional means, including solar power, rechargeable batteries or an AC adapter.

Any conventional actuator means may be employed, including use of a remove control switch.

Having described the invention in detail, those skilled in the art will appreciate that modifications may be made of the invention without departing frown its spirit.

Therefore, it is not intended that the scope of the invention be determined by the appended claims and their equivalents.

What is claimed is:

1. A shoe comprising;

a shoe upper;

a sole having a sole cavity opening within the sole;

a removable member intermediate the sole and sole cavity and a wearer's foot;

a motor assembly inserted at least partially into the cavity and releasably mounted within the sole cavity and having a generally flat surface to both support the removable member and transfer vibration from the motor assembly to the wearer's foot and the shoe through the removable member;

a battery operated vibrating means included with the motor assembly and located within the cavity; and an actuator switch.

2. The shoe as defined in claim 1 wherein the vibrating means is a motor having an off-center shaft mounted weight.

3. The shoe as defined in claim 1 wherein the vibrating means is a pulsation device.

4. The shoe as defined in claim 3 wherein the pulsation device further includes a frequency, pulse and amplitude regulation device.

5. The shoe as defined in claim 1 wherein the vibration transfer member further comprises an arch projection to enhance transfer of the vibrating means vibrations.

6. The shoe as defined in claim 1 wherein the actuator switch is integral to the vibration means.

7. The shoe as defined in claim 6 wherein an outer sole further comprises an aperture to allow the user access to the actuator switch.

8. The shoe as defined in claim 1 wherein the actuator switch consists of a magnetic switch in combination with a spring loaded magnetic plunger.

9. The shoe as defined in claim 1 wherein the vibrating means further includes a timer for providing a desired a duration of vibration produced by the vibrating means.

10. The shoe as defined in claim 1 wherein the vibrating means further comprises a self-cooling fan assembly, wherein the fan assembly disturbs air proximate the rotating shaft which acts to cool the vibration means and the surrounding space.

11. The shoe as defined in claim 1 further including a ventilation system to cool the user's foot, wherein the vibrating means includes a rotating shaft, wherein a portion of the rotating shaft disturbs air proximate the rotating shaft which acts to cool the surrounding space and therefore the user's foot proximate the space.

* * * * *